United States Patent [19]

Nishimaki et al.

[11] Patent Number: 5,130,244

[45] Date of Patent: Jul. 14, 1992

[54] STABLE AQUEOUS THROMBIN SOLUTION

[75] Inventors: Hideo Nishimaki, Kashihara; Kenmi Miyano, Osaka; Shouju Kameyama, Yawata; Kazuo Takechi, Daito; Yoshiro Iga, Osaka, all of Japan

[73] Assignee: The Green Cross Corporation, Osaka, Japan

[21] Appl. No.: 229,037

[22] Filed: Aug. 5, 1988

[30] Foreign Application Priority Data

Aug. 5, 1987 [JP] Japan .................................. 62-196558

[51] Int. Cl.$^5$ ........................ A61K 37/547; C12N 9/96
[52] U.S. Cl. .................................... 435/188; 435/214; 424/94.3; 424/94.64
[58] Field of Search ................... 424/94.64, 101, 94.3; 435/188, 214

[56] References Cited

U.S. PATENT DOCUMENTS

| | | | |
|---|---|---|---|
| 2,433,299 | 5/1905 | Seegers | 424/94.3 |
| 4,696,812 | 9/1987 | Silbering et al. | 424/94.64 |

FOREIGN PATENT DOCUMENTS

| | | |
|---|---|---|
| 142059 | 5/1985 | European Pat. Off. . |
| 2081090 | 2/1982 | United Kingdom . |

OTHER PUBLICATIONS

Chemical Abstracts, vol. 107, No. 4, Jul. 27, 1987, p. 323.

Primary Examiner—Jacqueline Stone
Attorney, Agent, or Firm—Sughrue, Mion, Zinn, Macpeak & Seas

[57] ABSTRACT

A stable aqueous thrombin solution containing thrombin and a sugar and an amino acid as a stabilizer is disclosed. According to the present invention, there is provided a stable aqueous thrombin solution.

3 Claims, No Drawings

STABLE AQUEOUS THROMBIN SOLUTION

This invention relates to a stable aqueous thrombin solution.

Thrombin acts on fibrinogen to form fibrin, thereby exerting a blood coagulating effect. For this reason, thrombin is used clinically as a hemostatic agent for topical application in the field of surgery.

Since thrombin is very unstable as in aqueous solution, it is usually made into a lyophilized medical preparation, which is used after dissolving at the time of use. However, liquid preparations are advantageous as compared with the lyophilized preparations in that they can be easily administered without being dissolved in distilled water or other solvents for injection.

From such a viewpoint, there have been proposed in recent years various methods for preparing a stable aqueous liquid composition of thrombin. For example, Japanese Patent Application Kokai (Laid-Open) No. 56-39,782 proposes a method using an organic carboxylic acid, Japanese Patent Application Kokai (Laid-Open) No. 57-18,985 proposes a method using albumin and Japanese Patent Application Kokai (Laid-Open) No. 62-106,028 proposes a method using a buffer composition as a stabilizer, respectively.

However, these methods are still unsatisfactory and, up to the present, an aqueous liquid preparation of thrombin has not yet been put to practical use.

The object of this invention is to provide a stable aqueous thrombin solution.

The present inventors have made extensive studies to achieve the above-mentioned object and as a result found that thrombin can be kept stable even as an aqueous solution by using a sugar and an amino acid in combination as a stabilizer. After further studies based on the above finding, the present invention has been accomplished.

Thus, according to this invention, there is provided a stable aqueous thrombin solution containing thrombin and a sugar and an amino acid as a stabilizer.

The thrombin for use in this invention is not particularly limited so long as it has a biological activity or a physiological activity. Examples of suitable thrombin include those obtained by fractionation of plasma protein. Thus, there may be used thrombin prepared by making thromboplastin, snake venom, etc. act in the presence of $Ca^{2+}$ on prothrombin purified from human or bovine plasma. There may also be used a commercially available pharmacopeial thrombin.

Thrombin for use in this invention preferably has a specific activity in the neighborhood of 100 to 1,000 units/mg protein.

The concentration of thrombin in the thrombin-containing aqueous solution is preferably 50 to 5,000 units/ml, particularly preferably 100 to 3,000 units/ml.

The pH of the thrombin-containing aqueous solution is preferably 5 to 8, more preferably 6 to 7. To maintain such a pH, the use of buffer solutions is preferable. Examples of suitable buffer solutions include phosphate buffer solution and citrate buffer solution.

In this invention, a sugar and an amino acid are used in combination to heighten the stability of thrombin.

There is no particular restriction as to the sugar used as a stabilizer in this invention. Examples of suitable sugars are monosaccharides such as glucose and mannose; disaccharides such as maltose, sucrose and lactose; sugar alcohols such as sorbitol, mannitol and xylitol, which may be used alone or in combination.

The quantity of sugar to be added is, for example, 1 to 20% (w/v), preferably 2 to 10% (w/v), for a solution containing 50 to 5,000 units of thrombin per milliliter.

The symbol "%(w/v)" means herein a percentage of a solute by weight per a solution by volume.

The amino acid for use in this invention is not particularly limited. Preferred examples thereof include neutral amino acids such as glycine, serine and threonine; acidic amino acids such as aspartic acid and glutamic acid; and basic amino acids such as arginine and lysine, which may be used alone or in combination.

The quantity of the amino acid to be added is, for example, 1 to 10% (w/v), preferably 1 to 5% (w/v), for a solution containing 50 to 5,000 units of thrombin per milliliter.

The stable aqueous thrombin solution of this invention may also contain other conventional additives.

The stabilizer comprising a sugar in combination with an amino acid for use in this invention significantly stabilizes thrombin.

In this invention, an aqueous solution containing thrombin and the stabilizers is prepared so as to meet the requirements described above using known techniques. The aqueous solution is then subjected to dialysis, sterile filtration, dispensation into vials, etc. according to conventional techniques of preparation. Thus, a stabilized aqueous solution (medical preparation) of thrombin is obtained.

According to this invention, there is provided a stable aqueous thrombin solution (medical preparation) which can keep its appearance and properties satisfactorily even after long-term storage.

This invention will be further described in more detail below with reference to the following Examples and Experimental Example. However, this invention is in no way limited by these Examples.

EXAMPLE 1

Prothrombin was purified from normal human plasma by means of barium chloride adsorption and DEAE-Sephadex column chromatography [Bajaj, S.P. et al., J. Biol. Chem., 248, 7729(1973)]. The prothrombin obtained above was mixed with thromboplastin prepared from human placenta, human plasma and calcium chloride solution and subjected to thrombin conversion to give crude thrombin (thrombin activity per 1 mg protein: 10 units). The crude thrombin was purified by SP-Sephadex column chromatography [Lundblad, R. L., Biochemistry, 10, 2501 (1971)]. The purified thrombin was concentrated and then dialyzed against a 100 mM citrate buffer solution (pH 7.0) containing 7.5% of D-mannitol by an ultrafiltration system (PELLICON®)to obtain a thrombin solution (3,500 units/ml, thrombin activity per 1 mg protein; 500 units).

To 45 ml of the thrombin solution obtained above were added 65 g of sucrose and 27 g of arginine [final concentration: thrombin 1,500 units/ml, sucrose 65% (w/v), arginine 27% (w/v)] and the resulting solution was adjusted to pH 5.9 with sodium hydroxide. The solution was heat-treated at 60° C. for 20 hours and then dialyzed against 0.1M citrate buffer solution (pH 6.7) by an trafiltration system (PELLICON®). The dialyzed solution was concentrated and filtered to obtain 105 ml of an aqueous thrombin solution [containing 1,100 units/ml of thombin, 7% (w/v) of sucrose and 4.7% (w/v) of arginine; pH 6.7].

The aqueous thrombin solution was stored at 5° C. for one month. Then the appearance, thrombin activity, behavior in cellulose acetate membrane electrophoresis and gel filtration were examined. No marked change was observed in these test items, revealing that thrombin was stable in the test.

EXAMPLE 2

Five thousand units of thrombin of official grade (Pharmacopeia of Japan) was dissolved in 10 ml of a phosphate buffer solution (pH 7). Then, sorbitol and glycine were added as a stabilizer to the resulting solution in a concentration of 5% (w/v) and 1% (w/v), respectively, to obtain an aqueous thrombin solution.

This aqueous thrombin solution was also excellent in storage stability compared to that of Example 1.

EXPERIMENTAL EXAMPLE 1

The aqueous thrombin solution obtained in Example 1 was used in order to examine the stability in long-term storage. The aqueous thrombin solution was stored at 5° C. for one month. Comparisons were made under 4 different stabilizing conditions, namely, no addition, sugar alone, amino acid alone, and both sugar and amino acid in combination. Table 1 shows the results of the examination.

TABLE 1

| | Stabilizer | | Percentage residual thrombin |
|---|---|---|---|
| | Sucrose | Arginine | (%) |
| After storage | — | — | 5 |
| | 7% (w/v) | — | 58 |
| | — | 4.6% (w/v) | 46 |
| | 7% (w/v) | 4.6% (w/v) | 95 |
| Before storage | | | 100 |

What is claimed is:

1. A stable aqueous thrombin solution containing thrombin and a disaccharide and an amino acid as a stabilizer, a quantity of the disaccharide being 2 to 10% (w/v) for a solution containing 50 to 5,000 units of thrombin per milliliter, wherein the disaccharide is sucrose and the amino acid is arginine.

2. A stable aqueous thrombin solution according to claim 1 which has a pH of 5 to 8.

3. A stable aqueous thrombin solution according to claim 1, wherein a quantity of amino acid is 1 to 10% (w/v) for a solution containing 50 to 5,000 units of thrombin per milliliter.

* * * * *